United States Patent [19]

Chow et al.

[11] Patent Number: 5,009,998

[45] Date of Patent: * Apr. 23, 1991

[54] METHOD FOR PERFORMING HETEROGENEOUS IMMUNOASSAY

[75] Inventors: Allan T. Chow, Wilmington, Del.; Michael A. G. Luddy, West Chester, Pa.

[73] Assignee: E. I. Du Pont de Nemours and Company, Wilmington, Del.

[ * ] Notice: The portion of the term of this patent subsequent to Nov. 20, 2007 has been disclaimed.

[21] Appl. No.: 115,506

[22] Filed: Nov. 3, 1987

Related U.S. Application Data

[63] Continuation-in-part of Ser. No. 66,583, Jun. 26, 1987, abandoned.

[51] Int. Cl.$^5$ .................. G01N 33/53; G01N 33/543; G01N 33/545; C12N 11/00
[52] U.S. Cl. .................... 435/7.92; 435/174; 435/177; 435/180; 435/7.94; 436/501; 436/518; 436/527; 436/538; 436/529; 436/531; 436/807; 436/810; 436/824; 436/825
[58] Field of Search ............... 436/518, 527, 531, 534, 436/524, 525, 526, 529, 533, 806, 807, 808, 809, 810, 528, 529, 530, 531; 435/7, 181; 530/413, 415; 210/606, 633, 663, 666, 687

[56] References Cited

U.S. PATENT DOCUMENTS

| 4,098,876 | 7/1978 | Piasio et al. | 424/1 |
| 4,155,711 | 5/1979 | Zelagin et al. | 436/810 |
| 4,200,436 | 4/1980 | Mochida et al. | 23/230 |
| 4,297,104 | 10/1981 | Claude | 436/807 |
| 4,376,110 | 3/1983 | David et al. | 436/513 |
| 4,745,073 | 5/1988 | Forrest et al. | 436/518 |

FOREIGN PATENT DOCUMENTS

| 1020866 | 1/1986 | Japan | 436/518 |

OTHER PUBLICATIONS

Methods in Enzymology, XL, 149, Ed. K. Mosbach, Academic Press, (1976).
Morrissey, B. W., Annals of the New York Academy of Sciences, 283, 50-64, (1977).
J. Colloid and Interface Science, vol. 76, No. 1, 254-255, (1980).
C. J. Van Oss et al., Sep. Purif. Methods, vol. 7, 245, (1978).
C. J. Van Oss et al., Sep. Sci. Technol., vol. 14, 305, (1979).

Primary Examiner—Esther L. Kepplinger
Assistant Examiner—Florina B. Hoffer

[57] ABSTRACT

The method described coats the interior of a tube-like support with the binding partner of the analyte. Analyte and anti-analyte-label conjugate are added. When the tube-like support is rotated end-over-end, the thin layer of analyte and conjugate readily react with the binding partners to form an immobilized label complex. When rotation stops, the reaction quenches to provide precise timing. The label complex is released and measured.

3 Claims, 2 Drawing Sheets

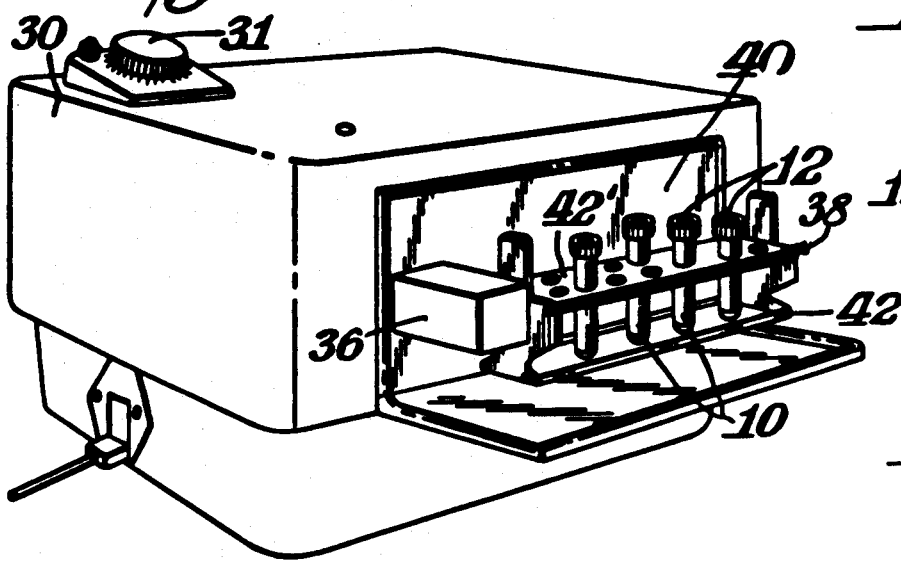
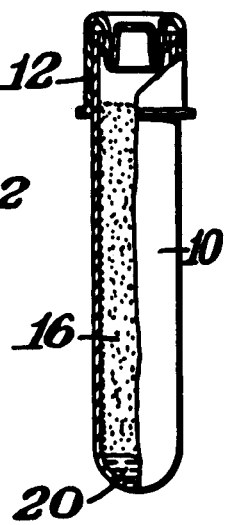
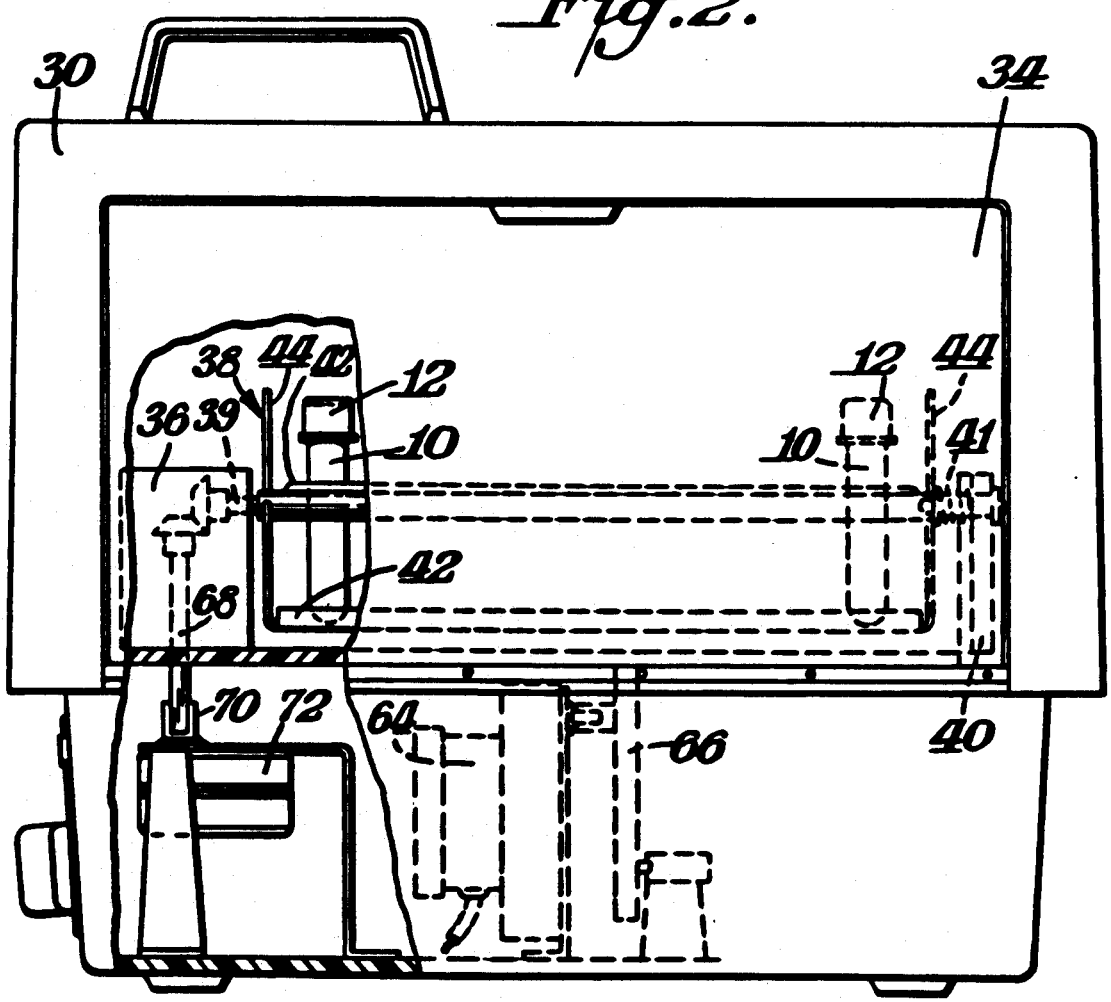

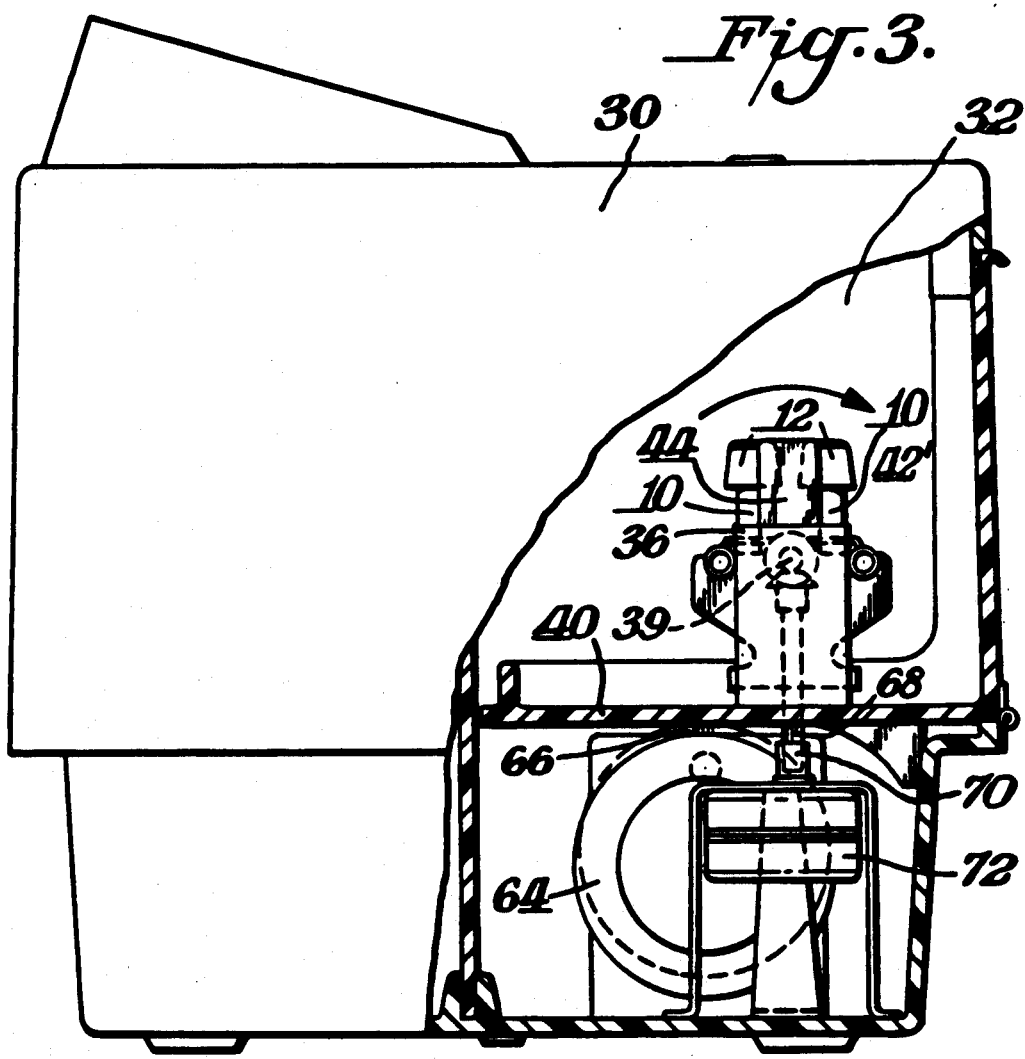
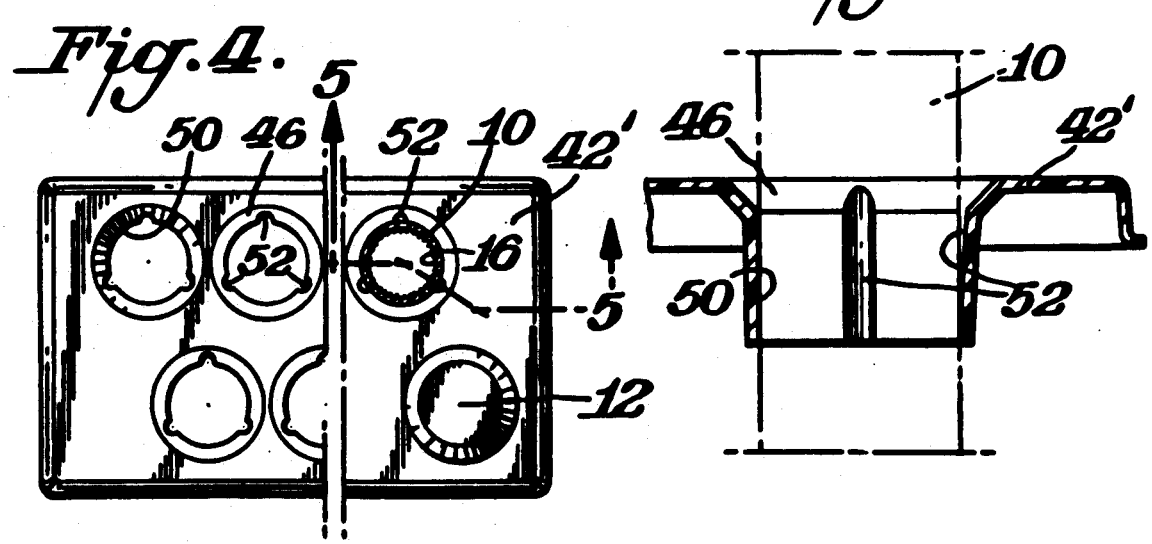

METHOD FOR PERFORMING HETEROGENEOUS IMMUNOASSAY

This application is a continuation-in-part of an application entitled "Heterogeneous Immunoassay", Ser. No. 066,583 filed June 26, 1988 now abandoned, entitled Heterogeneous Immunoassay, by Michael A. G. Luddy (IP-0684).

TECHNICAL FIELD

This invention relates to a method and apparatus for performing heterogeneous immunoassays and more particularly to a method and apparatus for performing heterogeneous immunoassays in a precisely controlled manner.

BACKGROUND OF THE INVENTION

In recent years a number of immunoassay techniques have been developed for the measurement of clinically important ligands. Typically a competitive binding immunoassay utilizes a conjugate of a labeling substance and a binding component which participates in a binding reaction to produce two species of labeled complexes a bound species and a free species. The relative amounts of the labeled complexes are a function of the amount of the ligand to be detected in the test sample.

Where the labeling substance in the bound species and in the free species are substantially indistinguishable by the means used to measure the labeling substance the bound and the free species must be physically separated. This type of assay is referred to as heterogeneous.

The two most widely used heterogeneous immunoassays are the radioimmunoassay (RIA) and the enzyme linked immunosorbant assay (ELISA). In the RIA, a sample containing an unknown amount of antigen is mixed with a known amount of radiolabeled antigen and antibody. The assay components are allowed to react to near-equilibrium and then the antibody-bound antigen is separated from the unbound antigen. Since sample antigen competes with the labeled antigen for a limited number of antibody binding sites, the more antigen in the sample, the less labeled antigen is in the bound fraction (or the more is in the unbound fraction). This type of assay is generally time-consuming (1-3 hours) and labor intensive.

RIA suffers from two major disadvantages: First, the labeling substance employed is a radioisotope which poses numerous problems associated with handling, storage, and disposal. Second, RIA is performed in a competitive mode (i.e., the analyte and the labeled analyte compete for a limited number of binding sites on the antibody), and, therefore, the antibody affinity constant limits the sensitivity of the assay, typically in the range of $10^{-8}M^{-1}$ to $10^{-11}M^{-1}$.

ELISA is similar in principle to RIA except that the labeling substance is an enzyme rather than a radioisotope. Other labeling substances have been described in addition to isotopes and enzymes. These include fluorophores coenzymes bioluminescent materials, and enzyme inhibitors. All suffer from the limitation that sensitivity is a strict function of the antibody affinity constant.

Various methods of effecting the separation step in heterogeneous immunoassays are known. These include filtration, centrifugation and chromatography.

U.S. Pat. No. 3,654,090, issued Apr. 4, 1972, to Schuurs et al., describes a noncompetitive heterogeneous immunoassay for human chorionic gonadotropin (HCG) which uses an excess of enzyme-labeled divalent antibody and an immobilized HCG column to accomplish the separation step.

U.S. Pat. No. 4,200,436, issued Apr. 29, 1980 to Mochida et al., discloses an immunoassay employing a labeled monovalent antibody in which immobilized antigen (the same antigen as that to be measured) is used to separate the free labeled antibody from the labeled antibody-antigen complex. Since it is primarily the bound fraction which is measured, this assay is usually performed in a competitive mode. Hence, sensitivity is limited by the affinity constant of the antibody when the assay is performed according to the preferred mode.

U.S. Pat. No. 4,098,876 issued July 4 1978, to Piasio et al., discloses a reverse sandwich immunoassay in which the analyte is incubated with labeled antibody prior to incubating with the immobilized second antibody. After separation of the bound, labeled complex from the incubation medium the bound label is measured.

U.S. Pat. No. 4,376,110, issued Mar. 8, 1983, to David et al.. discloses the use of monoclonal antibodies in a two-site sandwich immunoassay format. The preferred mode disclosed involves the measurement of the bound label after separation from the free label.

The preferred mode of operation of the heterogeneous immunoassay techniques described above is to utilize excess primary labeled binding partners and/or excess bound, secondary binding partners to enhance the speed, sensitivity and precision of the assay. When operating in this preferred mode, it becomes necessary to measure the activity of the bound label since there is generally too much free label to allow accurate detections of the small decrease in the amount of free label. The detection of bound label is particularly difficult in some automated analyzers where it is often necessary to introduce the sample to the analyzer in a liquid form.

Materials such as proteins protein-hapten conjugates and specifically antibodies can be adsorbed onto the surface of solid or liquid supports such as polyethylene, polycarbonates, perfluorocarbon polymers, latex particles, glass, and magnetic particles with polystyrene being preferred. In general this adsorption is considered to be irreversible even in the presence of surfactants, chaotropes denaturants such as 8M urea or guanidine hydrochloride. [Methods in Enzymology XL, 149 Ed. K. Mosbach, Academic Press (1976): Morrissey B. W., Annals of the New York Academy of Sciences, 283, 50-64 (1977)].

While proteins are thought to be irreversibly bound under many aqueous conditions, some solvents may cause desorption from hydrophobic surfaces. For example, dimethylsulfoxide (DMSO) and tetrahydrofuran (THF) have been used in hydrophobic chromatography to desorb proteins that were adsorbed from aqueous solution onto hydrophobic supports, presumably by changing the van der Waals or London forces between the protein and the support. These solvents, however, often attack and dissolve organic supports and, at least in the case of DMSO, denature many proteins such as enzymes. [J. Colloid and interface Science, Vol. 76, No 1. 254-255 (1980); C. J. Van Oss et al., Sep. Purif. Methods, Volume 7, 245 (1978); C. J. van Oss et al., Sep. Sci. Technol., Volume 14 305 (1979)].

When the walls of a solid support, such as provided by tubular containers formed of polyethylene, polycarbonates, perfluorocarbonpolymers or glass or the like, are coated with protein-hapten conjugates or antibodies such materials are bound to the surface of the solid support. As described by Luddy, these materials can be released from the solid support surface after they have formed a labeled complex during the immunoassay. The release is accomplished by the use of a release agent which may be monovalent or divalent salts or an organic base. Even using this release procedure, immunoassays of this type tend to be inaccurate due to (a) lack of proper timing of the reaction, (b) improper incubation temperatures and (c) the relatively low diffusion rates of the biological material of interest in the analyte. This biological material must become bound to the proteinaceous binding partner of the analyte which can only occur by contact. Timing is particularly important because of the capture reaction is not allowed to go to completion. Because of the volume of the analyte, proper contact can be difficult to achieve thus rendering accurate timing of the reaction a problem if uniform results are to be obtained. Also the reactions must be terminated at a controllable time. This is often accomplished by introducing a quenching reagent to completely stop the reaction, but this can interfere with the assay and add to the problem of separating the bound and unbound components.

U.S. Pat. No. 3,801,467 describes an apparatus for providing temperature gradients for the culturing of microorganisms. A central thermal conductive bar is positioned to contain a plurality of test tubes glass rods, petri dishes and any other growth chamber necessary. One end of the bar is connected to a heat source and the other a cooling source to provide a thermal gradient along the length of the bar. This bar is rotatable about its axis via a crank/motor. There is no mention of quenching the reaction.

U.S. Pat. No. 3,535,208 describes an apparatus for providing a temperature gradient for culturing microorganisms. In this device however a shaker table is used external to the gradient box. Fluid is circulated through the two triangular shaped volumes - the fluids are at different temperatures creating a linear gradient along the length of the box. There is no mention of quenching the reaction.

U.S. Pat. No. 3,832,532 describes a method and apparatus for testing antibody susceptibility. Included in the device, is the incubator/shaker apparatus shown in FIGS. 22 and 23. Three racks 54 hold ten cuvettes in the chamber that is held at 36° C. These trays are rotated on the platform 58 at 220 rpm at a ¼ inch amplitude. There is no capability for automatic quenching.

There is a need for an improvement of heterogeneous immunoassays wherein the time temperature and contact rate of the reaction components are better controlled.

SUMMARY OF THE INVENTION

Many of the disadvantages of the prior art heterogeneous immunoassays are overcome by the method and apparatus of this invention which precisely controls the time as well as the temperature of a reaction in which an analyte is bound to a proteinaceous binding partner of the analyte which is bound to the walls of a container. The reaction time is controlled both as to exposure time of the coating on the solid support to the analyte and by reducing the diffusion time required for the analyte to contact to coating.

This invention is a method of performing a heterogeneous immunoassay on a sample for the determination of a biological analyte using a solid support defining a container capable of the reversible immobilization of binding partners of the analyte, comprising the steps of: coating at least a portion of the interior of the container with a binding partner of the analyte, introducing the sample and an analyte-receptor label conjugate into the container, capping the container aqitating the container in a controlled temperature environment for a controlled time to subject substantially all of the interior of the container to the sample and conjugate to form a label complex bound to such coating, releasing the label complex from the coating, and measuring the activity of the label.

In a preferred aspect of the method the volume of the sample and conjugate is small relative to the volume of the container and following agitation of the container, the container is oriented vertically such that the sample and conjugate contact only a reduced portion of the coating thereby to effectively attenuate or stop most of the assay reaction. At the same time, the sample and conjugate are placed in a lower temperature environment to slow the reaction kinetics.

In an alternative embodiment, the upper portion of the container is uncoated and the container is vertically oriented following agitation upside down with the lower portion above the upper portion of the container so as to reduce contact between the analyte and the coating.

In still another alternative, the container is turned upside down and the analyte and conjugate allowed to enter a cavity formed in the cap of the container thus preventing all further reaction between the analyte and the coating.

A preferred apparatus for performing the method of this invention includes an incubation chamber having a door which permits a rack holding sample containers to be positioned either inside or outside the chamber. When the rack is positioned inside the chamber, a motor rotates the rack about its longitudinal axis such that the tubes are rotated end-over-end to effect contact between a thin layer of the sample and conjugate materials with the coating. Since the layer is relatively thin diffusion time is not a significant factor and all portions of the analyte and conjugate have good access to the coating to form the labeled complex. The same incubation chamber can be used to assist in releasing the labeled complex from the support. The assay itself may be determined using any conventional photometric techniques or other label detecting technique.

BRIEF DESCRIPTION OF THE DRAWINGS

The invention may be more fully understood from the following detailed description thereof taken in connection with accompanying drawings which form a part of this application and in which:

FIG. 1 is a pictorial representation of an incubation chamber used to effect the method of this invention;

FIG. 2 is a front elevational view partially cut away of the incubation chamber of FIG. 1 particularly showing the gears by which the rack is rotated;

FIG. 3 is a side elevation view of the incubation chamber of FIG. 1 partially cut away to depict a portion of the rack and its drive mechanism:

FIG. 4 is a fragmentary plan view of the rack of FIG. 1 showing the contacts used to facilitate the positioning of the solid support tubes within the rack;

FIG. 5 is a cross-sectional site elevation view of the rack of FIG. 4, taken along the section line 5—5 to slow the contacts;

FIG. 6 is an elevation view, partially cut away, of a coated support tube having a hollow cap used with this invention.

DESCRIPTION OF THE PREFERRED EMBODIMENT OF THE INVENTION

In general, the immunoassay of this invention can be used with any of the currently known heterogeneous immunoassay techniques in which it is desired to measure the amount of label on the immobilized phase. These include the standard ELISA, sandwich, and reverse sandwich assay techniques. The only requirement is that the binding partner such as an antibody which is immobilized on the solid phase be reversibly bound to it. The instant invention can be used with a variety of binding partners and will be exemplified through the use of antibodies. Any antibody such as polyclonal, monoclonal, whole and fragmented antibodies can be used.

The adsorption of proteins or other macromolecules useful as immobilized binding partners in heterogeneous immunoassays and their complexes can be achieved through the use of the release reagents. The release reagents of this invention are high ionic strength solutions and include salts, such as divalent metals and especially salts of magnesium, monovalent salts such as sodium chloride, or organic bases such as 2-amino-2-methyl-1-propanol, trihydroxymethylaminomethane and, preferably, diethanolamine (DEA) or both. The selection of release reagent is concentration dependent; high concentrations of either or lower concentrations of both can suffice. Minimum levels can be determined functionally. At low, buffer-type concentrations the salts and organic bases do not act as release reagents. In addition, ionic and non-ionic surfactants, such as sodium dodecyl sulfate (SDS), alkylaryl polyether alcohol and polyoxyethylene sorbitan monolaurate can also be included.

The preferred composition of the release reagent is 1.0 M DEA, 0.1 mM $MgCl_2$, and 0.5% Tween 20 pH 8.9, although a wide rang of pH, $Mg^{+2}$, and Tween 20 concentrations are effective.

The exact composition of the release reagent has to be selected to be compatible with the label of the binding partner while also being effective for the release of the complex from the solid support. For example, if acid is a denaturant for the label, then a neutral or basic release reagent should be used. For example when the label is alkaline phosphatase a pH of 8.9 is preferred and when the label is $\beta$-galactosidase a pH of 7.6 is preferred.

In the event the coated immobilizing support is not utilized within a short time period after its preparation, approximately 1 hour, the solid immobilized bearing the immobilized binding partner needs to be kept in contact with a phosphate buffered saline optionally containing BSA. The BSA content can range from 0.05-30%. If the solid phase is allowed to dry out, the immobilized binding partner will not completely release (desorb) in the presence of the release reagents of the invention. BSA functions to increase long-term stability of the proteins immobilized on the support. It is expected that other proteins can function similarly to BSA.

Any detectable label can function in the immunoassay of this invention. These include enzymes, radioisotopes, luminescent materials, fluorophores, coenzymes, enzyme inhibitors and enzymes. The latter are preferred.

Any suitable materials can serve as a support for reversible immobilization of the proteins used for the capture of the biological material of interest. The immobilizing supports c an be solid or liquid and include polystyrenes, polyethylenes, polycarbonates, perfluorocarbon polymers glass, coated magnetic particles and a variety of latex particles. The support is not only capable of carrying the protein binding partner of the biological material of interest but also the complex formed between the binding partner and the material of interest (often referred to as the analyte) and any further complexes (often taking the form of a double complex referred to as a "sandwich"), collectively referred to as the complex. When treated with the release reagent of this invention the immobilized label complex is removed from the support permitting the subsequent liquid phase determination of the label present on one of the members of the complex. This ability to remove the immobilized labeled complex when desired permits an immunoassay to be accomplished under tightly controlled time and temperature conditions.

According to a preferred embodiment of this invention, the solid support for an immunoassay is in the form of a container 10 (FIG. 6) shaped like test tube, closed at one end and open at the other. A cap 12 is provided for the tube which cap may be formed of polypropylene or other suitable material that does not react with the conjugate and is shaped to close off or seal the container 10. Preferably the cap interior is hollowed out to accommodate fluids from the container when the container is placed upside down. The fluids may be contained within the hollow portion of the cap (and alternatively the upper portion of the container itself). The interior of the container is coated 16 with a reversibly immobilized proteinaceous binding partner of the analyte to be assayed, the analyte being a biological material of interest. If a hollow cap 12 is not used, the coating preferably is attached or secured only to the lower portion of the container 10 such that if the container is placed upside down any fluids therein will no longer contact the coating. The volume of the container is much larger than the combined volumes of the sample and assay conjugate. The container typically may have a volume of 7.5 mL. By way of comparison the combined volume of the sample and enzyme conjugate typically is 1.0 mL as will be described below. As will be described this is to facilitate quenching or attenuation of the assay reaction thereby to control the time thereof.

The container 10 forming the solid support is coated at room temperature using PBS (phosphate buffered saline) pH6, containing 10 micrograms per mL of the binding partner of interest, usually an antibody. After one hour of incubation, the tube is washed three times with PBS containing 0.1% bovine serum albumin pH 7 6. Finally, the coated container is filled with PBS containinq 0.1% BSA, pH 7.6. This solution is discarded before the start of the immunoassay procedure. After decanting, a known volume of patient sample, usually 500 $\mu$L of serum containing an unknown amount of analyte, is mixed with 500 $\mu$L of an anti analyte-label conjugate in the coated polystyrene tube.

According to the assay method of this invention a coated container 10, filled with PBS as described, is emptied of PBS and after removal of the container cap 12, the analyte serum and anti-analyte label conjugate are added. These fluids are mixed and the cap replaced. Mixing is accomplished preferably by rotating the container end-over-end for 20 minutes at a temperature most suitable for the particular assay being performed. The container is emptied and washed. A release reagent is added to strip the complex from the wall. A color substrate is added. The color is measured with any suitable instrumentation such as the aca ® discrete clinical analyzer (a registered trademark of E. I. du Pont de Nemours and Company, Wilmington, DE). Using the aca ® analyzer a known volume of the release solution is automatically injected into an analytical test pack (described in U.S. Patent Re. 29,725 to Johnson et al., and reissued August 8, 1978 incorporated herein by reference) in the filling station of the instrument, followed by a volume of buffer sufficient to bring the final in-pack volume to 5 μL. The pack is automatically processed at 37° C. with addition of the substrate reagent required for the signal generating reaction at either breaker/mixer I or breaker/mixer II and photometric readout of the signal.

It is important that the assay capture reaction occur at a uniform rate and be quenched after a precise amount of time. This is accomplished with the method of this invention, by coating a large portion of the interior of the container 10 relative to the volume of the sample and conjugate liquids 20 placed therein, the liquids have access to the sidewall coating only during agitation. Furthermore because of the end-over-end agitation, only a thin layer of liquid will contact or cover the walls of the tube during agitation and hence the coating 16. Because of this thin layer the diffusion time required for all portions of the liquids to come into contact with the coating is not a significant factor and in fact is greatly reduced. In any event, reaction time is accurately controllable. When the time for reaction is complete, the agitation is stopped and the labeled conjugate allowed to remain in the bottom of the container. Since the portion of the sample and conjugate liquids contacting the coated wall portion is relatively small compared to the entire interior of the walls of the container the reaction is attenuated and effectively stops.

In an alternative method, the coating is not permitted to continue all the way up the walls of the container 10 so that when it is desired to quench the reaction it is simply necessary to invert the container and allow all of the liquids to drain to the top portion of the container and thereby be removed from the coated region. The cap may then be removed, the sample discarded and the label complex when removed from the container wall transferred to a measuring container.

Alternatively, the complex need not be stripped and substrate may be added to develop the color and the color measured.

An apparatus for effecting the method of this invention is depicted in FIGS. 1-5 inclusive. There may be seen therein a housing 30 containing an incubation chamber 32 (FIG. 3) in which the temperature may be controlled by any conventional means. The chamber is preferably maintained at 37° C. although if desired an adjustable temperature control of known design may be used. In accordance with this invention, the front wall of the housing 30 includes a door 34 which may be opened forward 90°. A bevel gear housing 36 secured to the door 34 mounts a test rack 38 for rotation about the longitudinal axis of the test rack. The test rack may be formed of sheet plastic materials driven directly by the shaft 39 of one of the bevel gears in the beveled gear housing 36. The test rack is pivotally supported by the bevel gear shaft 39 at one end and by a spring loaded pin 41 positioned in an upright 40 at the other end. The upright is secured to the door. The test rack 38 is formed by upper piece of sheet plastic 42' positioned by a U-shaped piece of sheet metal 42 having uprights 44 which support the upper piece 42'. The uprights 44 engage the shaft 39 and pin 41, respectively. The upper plastic plate 42 has holes 46 formed therein to accommodate containers 10 (test tubes preferably) formed of the materials described above, each container having a cap 12. Each of the holes 46 has its inner rim used to support sector-like contacts 50 separated by outwardly tapered grooves 52 which grip the containers 10. The upper piece is formed of any suitable plastic such as polyethylene terephthalate.

A timer 31 may control the time during which operation occurs as mentioned. Time is initiated by an on-off switch on the timer. When the on-off switch is actuated a motor 72 acting through the bevel gears initiates rotation of the bracket 40, and hence the test rack 38 about its longitudinal axis causing containers 10 to rotate end-over-end thereby agitating the liquids contained therein and causing them to contact the walls of the tubes with a thin layer of the liquids therein. The design of the bevel gears is such that when the door 34 is closed one bevel gear shaft 68 engages a slot 70 driven by a motor 72 which effects such the rotation. When time is complete a cam motor 64 acting through a cam 66, which contacts a folded portion of the front door 34, opens the door. The door completes its opening by gravity.

With the precise timing permitted by the incubation chamber together with the use of small quantities of liquids within each container, quenching or attenuation of the reaction may be effected very quickly by any of the several methods noted hereinbefore. Thus the timing of the reaction is controlled very actively and precisely. Furthermore excellent contact is made with the coating in a manner such that the fusion time of the analyte and conjugate to the coating is reduced to a minimum.

We claim:

1. A method of performing a heterogeneous immunoassay on a sample for the determination of a biological analyte, using a solid support defining a container capable of the reversible immobilization of binding partners of the analyte, comprising the steps of:
   coating substantially all of the interior of the support with a binding partner of the analyte,
   introducing the sample and an anti-analyte-label conjugate into the support,
   capping the support,
   agitating the support end-over-end in a controlled temperature environment for a controlled time to subject substantially all of the interior of the support to a thin layer of the sample and conjugate to form a labelled complex bound to such coating, thereby to reduce the diffusion time required for all portions of the sample and anti-analyte-label conjugate to come in contact with the support, separating non-reacted components of the sample and anti-analyte-label conjugate from the support,
   releasing the label complex from the coating using salts or organic bases, and
   measuring the activity of the label.

2. The method of claim 1 wherein the support has an upper end and the method includes the steps of capping the upper end with a cap defining a cavity, and orienting the support following agitation such that contents of the support flow into the cavity, thereby to stop the assay reaction.

3. The method of claim 2 wherein the support is a tube and is vertically oriented following agitation.

* * * * *